US 7,837,622 B2

(12) United States Patent
Itoh et al.

(10) Patent No.: US 7,837,622 B2
(45) Date of Patent: Nov. 23, 2010

(54) RECORDING MEDIUM AND BLOOD GLUCOSE MONITORING SYSTEM USING THE RECORDING MEDIUM

(75) Inventors: Takehito Itoh, Osaka (JP); Hideyuki Tomita, Otsu (JP)

(73) Assignee: Nipro Corporation, Osaka (JP)

( * ) Notice: Subject to any disclaimer, the term of this patent is extended or adjusted under 35 U.S.C. 154(b) by 1335 days.

(21) Appl. No.: 10/214,371

(22) Filed: Aug. 6, 2002

(65) Prior Publication Data
US 2003/0032077 A1 Feb. 13, 2003

(30) Foreign Application Priority Data
Aug. 10, 2001 (JP) .............................. 2001-243363

(51) Int. Cl.
A61B 5/00 (2006.01)
G01N 31/00 (2006.01)
G05B 21/00 (2006.01)

(52) U.S. Cl. .......................... 600/365; 702/22; 700/266
(58) Field of Classification Search .................. 702/19; 600/300; 707/101
See application file for complete search history.

(56) References Cited

U.S. PATENT DOCUMENTS

| 5,288,636 | A | * | 2/1994 | Pollmann et al. | ....... 204/403.14 |
| 5,307,263 | A | | 4/1994 | Brown | |
| 5,497,772 | A | | 3/1996 | Schulman et al. | |
| 5,507,288 | A | * | 4/1996 | Bocker et al. | ................ 600/322 |
| 6,024,699 | A | | 2/2000 | Surwit et al. | ................ 600/300 |
| 6,066,243 | A | * | 5/2000 | Anderson et al. | ......... 422/82.01 |
| 6,103,033 | A | * | 8/2000 | Say et al. | ..................... 156/73.1 |
| 6,192,891 | B1 | | 2/2001 | Gravel et al. | |

FOREIGN PATENT DOCUMENTS

| EP | 0 970 655 A1 | 1/2000 |
| EP | 1048310 | 11/2000 |
| JP | 02-006737 | 1/1990 |
| JP | 2-6737 A | 1/1990 |
| JP | 7311196 | 11/1995 |
| JP | 8-502590 A | 3/1996 |
| JP | 8-334489 A | 12/1996 |
| JP | 2000-60803 A | 2/2000 |
| JP | 2000-503556 A | 3/2000 |
| JP | 2000-139857 A | 5/2000 |
| JP | 2000-166881 A | 6/2000 |
| JP | 2000-258382 A | 9/2000 |
| JP | 2000-512414 A | 9/2000 |
| JP | 2000-354591 A | 12/2000 |
| JP | 2000356634 | 12/2000 |
| JP | 2001-78968 A | 3/2001 |
| JP | 2001-505337 A | 4/2001 |
| JP | 2002-531154 A | 9/2002 |
| WO | WO 94/29703 A1 | 12/1994 |
| WO | WO97/28736 | 8/1997 |
| WO | WO 97/28737 A1 | 8/1997 |
| WO | WO97/49077 | 12/1997 |
| WO | WO-98/32076 A1 | 7/1998 |
| WO | WO99/22236 | * 5/1999 |
| WO | WO-99/22236 | 5/1999 |
| WO | WO 00/32088 A1 | 6/2000 |
| WO | WO01/45014 | 6/2001 |

OTHER PUBLICATIONS

Sakakida et al., Biosensors and Bioelectronics, 1996, vol. 11, No. 11 (p. iii-iv).*
Yang et al., Biomedical Instrumentation and Technology, 1997, 31(1): p. 54-62.*

* cited by examiner

Primary Examiner—Marjorie Moran
Assistant Examiner—Pablo Whaley
(74) Attorney, Agent, or Firm—Birch, Stewart, Kolasch & Birch, LLP

(57) ABSTRACT

A recording medium includes a sensor circuit unit generating a current in accordance with a blood glucose level in blood, and a control unit calculating blood glucose level data from the data obtained by digital conversion of the generated current at signal processing unit, writing the calculated data to an EEPROM as a memory unit, reading the blood glucose level data from EEPROM and transmitting the same to a portable terminal on which recording medium is mounted, through a communication control unit. The recording medium further includes a power supply control unit receiving power from the portable terminal on which the recording medium is mounted, and supplying power to various portions in the recording medium. As a result, the recording medium can be utilized, when mounted on the portable terminal, a blood glucose monitoring apparatus, and the recording medium can be used in a system for providing bi-directional service between the portable terminal and a server managing the blood glucose information received from the portable terminal connected by a network.

14 Claims, 7 Drawing Sheets

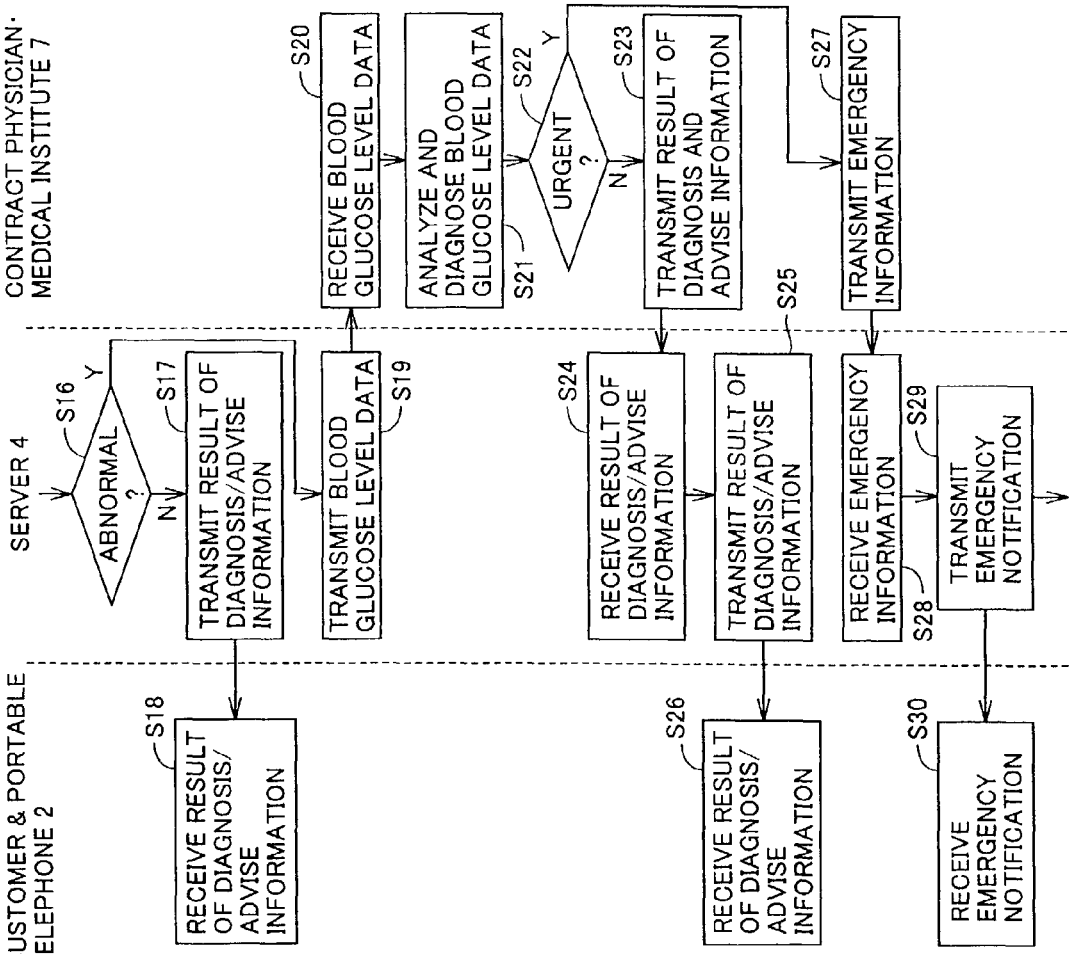

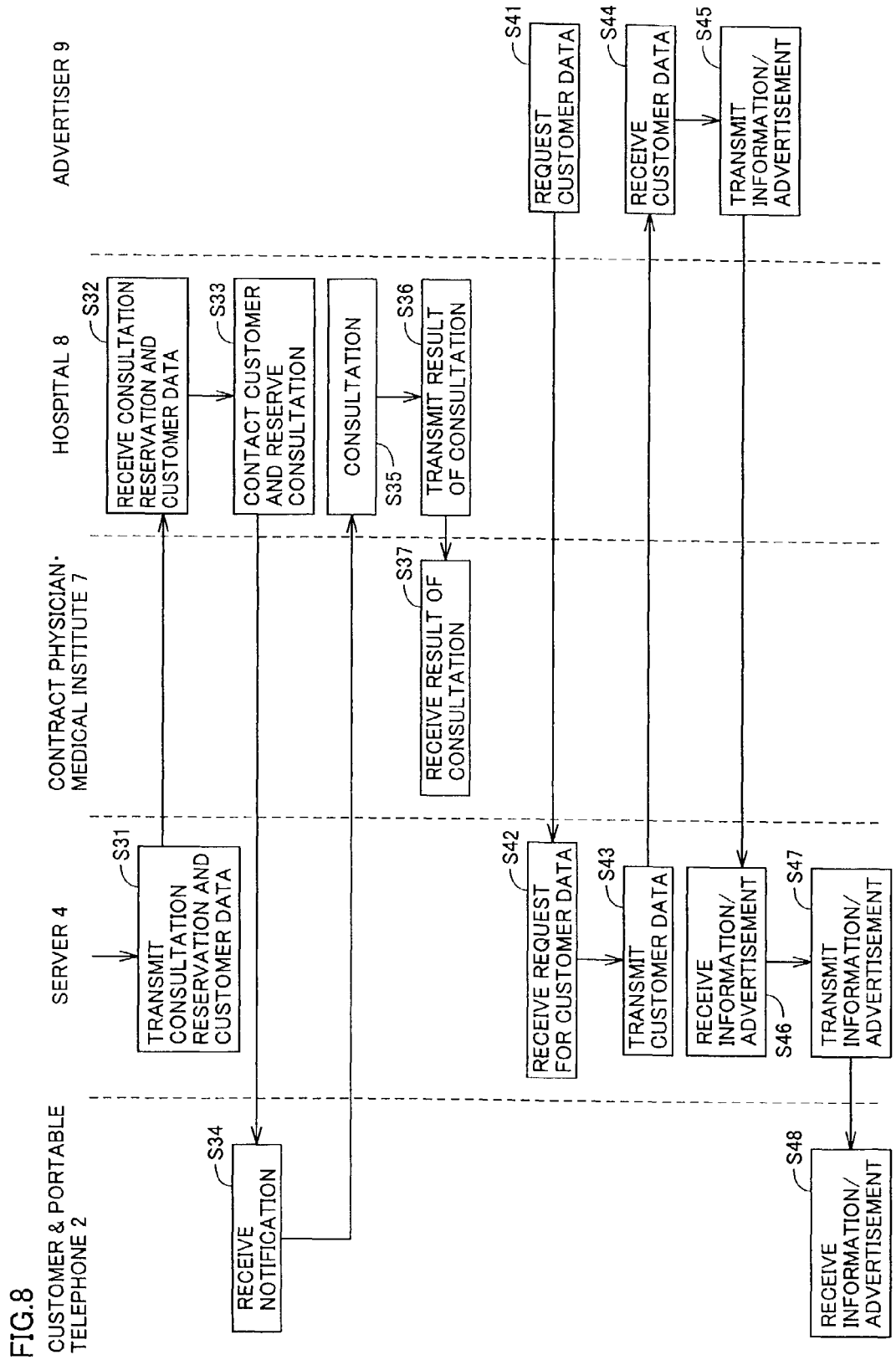

RECORDING MEDIUM AND BLOOD GLUCOSE MONITORING SYSTEM USING THE RECORDING MEDIUM

BACKGROUND OF THE INVENTION

1. Field of the Invention

The present invention relates to a recording medium attached to a portable terminal and using the portable terminal as a blood glucose monitoring apparatus and to a blood glucose monitoring system. More specifically, the present invention relates to a recording medium attached to a portable terminal that can be connected to a network and using the portable terminal as a blood glucose monitoring apparatus that can be connected to the network, and to a blood glucose monitoring system.

2. Description of the Background Art

Control of blood glucose level is a basic treatment of diabetes. For proper control of the blood glucose level, it is necessary to monitor variation in blood glucose level on a day-to-day basis to see if the level is well controlled.

Recently, apparatuses for Self-Monitoring of Blood Glucose (SMBG) that enables monitoring of blood glucose level, which was possible only at a medical institution in the past, in a simple manner by the user become commercially available. Thus, it is possible to monitor the blood glucose level at home in a simple manner.

The apparatuses for self-monitoring of blood glucose can be roughly classified into ones that use electrode method in which taken blood is caused to react with a glucose oxidizing enzyme fixed on an electrode or a test paper, and a current resulting from the reaction is measured, and ones that use paper test in which the taken sample is put on a test paper, and the blood glucose level is measured from the degree of color change on the test paper.

Generally, most of the commercially available apparatuses for self-monitoring of blood glucose adopt the electrode method in view of measurement accuracy or the like.

Known apparatuses of self-monitoring of blood glucose using the electrode method include various types such as the type in which skin is punctuated by a puncturing device with a puncture needle, blood sample thus obtained is put on a test paper, and the test paper is mounted on a monitoring apparatus for monitoring, the type in which puncturing and monitoring functions are integrated, and the non-invasive type that utilizes gingival crevice fluid or near-infrared lay to eliminate the necessity of the puncture needle.

Further, among the commercially available apparatuses for self-monitoring of blood glucose using the electrode method, some have a data output function enabling output of the data of measurement, so that, when connected to a dedicated connecting apparatus, the measurement data can be transmitted, for example, to a personal computer, enabling data management by the personal computer.

The above described apparatuses for self-monitoring of blood glucose are, basically, used as stand alone apparatuses. A user of the apparatus for self-monitoring of blood glucose controls his/her blood glucose level and manages the tendency of the blood glucose level, by dietetic therapy or by determining dose of insulin, based on the measured value displayed at a display unit of the apparatus for self-monitoring of blood glucose.

It is possible, however, that a patient of diabetes needs immediate consultation with a physician dependent on the result of measured blood glucose level, and further, there may be an emergency case that because of the abnormality in blood glucose level, physical condition of a patient so deteriorates that the patient cannot by himself/herself visit a hospital nearby, after he/she has measured the blood glucose level by the above described apparatus for self-monitoring of blood glucose.

In such a case, it is impossible to ask for immediate diagnosis by a physician, for example, when the user uses the apparatus for self-monitoring of blood glucose of the above described type. Even when the apparatus for self-monitoring of blood glucose that can be connective to a personal computer described above, a dedicated connector apparatus is necessary for connecting the self-monitoring apparatus with the personal computer. Therefore, it is impossible to cope with the above described urgent situation when the user is away from home.

The apparatuses for self-monitoring of blood glucose described above all require a display device for displaying measured values and a power supply battery for driving internal devices. Therefore, there is a problem that the apparatuses are large.

SUMMARY OF THE INVENTION

The present invention was made to solve the above described problems, and an object is to provide a recording medium capable of measuring blood glucose, which is mounted on a portable terminal to use the portable terminal as a blood glucose monitoring apparatus, and which is used in a system having the portable terminal and a server managing blood glucose level data received from the portable terminal connected to a network and providing bi-directional service between the terminal and the server.

Another object of the present invention is to provide a blood glucose monitoring system including a recording medium which is mounted on a portable terminal to use the portable terminal as a blood glucose monitoring apparatus and which is used in a system having the portable terminal and a server managing blood glucose level data received from the portable terminal connected to a network for providing bi-directional service between the terminal and the server, and the portable terminal to which the recording medium is mounted.

A still further object of the present invention is to provide a recording medium capable of blood glucose monitoring that is highly portable.

The present invention provides a recording medium operating mounted on a portable terminal capable of supplying power, including: a communication control unit exchanging data with the portable terminal; a sensor circuit unit generating a current in accordance with a blood glucose level of taken blood; a signal processing unit converting the generated current to a digital data and outputting the data; an electrically erasable and programmable non-volatile memory unit storing blood glucose level data converted based on the data output from the signal processing unit; a control unit converting the data output from the signal processing unit to the blood glucose level data, writing the converted data to the memory unit, reading the blood glucose level data from the memory unit and transmitting the data to the portable terminal through the communication control unit; and a power supply control unit receiving power from the portable terminal and supplying power to the sensor circuit unit, the signal processing unit, the memory unit, the communication control unit and the control unit.

Preferably, the portable terminal transmits through a communication network, measured blood glucose level data to a server that manages the blood glucose level of a customer.

Preferably, the portable terminal displays the measured blood glucose level data.

Preferably, the portable terminal is one of a portable telephone, a personal digital assistant and a portable personal computer.

According to another aspect, the present invention provides a blood glucose monitoring system including a portable terminal and a recording medium operating mounted on the portable terminal, wherein the portable terminal includes a first communication unit exchanging data with the recording medium, a power supply unit supplying power to the recording medium and a first control unit; the recording medium includes a second communication control unit exchanging data with the portable terminal, a sensor circuit unit generating a current in accordance with blood glucose level of obtained blood, a signal processing unit converting the generated current to digital data and outputting the digital data, an electrically erasable and programmable non-volatile memory unit storing blood glucose level data converted based on the data output from the signal processing unit, a second control unit converting the data output from the signal processing unit to the blood glucose level data and writing in the memory unit, reading the blood glucose level data from the memory unit and transmitting the read data to the portable terminal through the second communication control unit, and a power supply control unit receiving power from the portable terminal and supplying power to the sensor circuit unit, the signal processing unit, the memory unit, the second communication control unit and the second control unit; and the first control unit controls the first communication control unit when the blood glucose data is received from the recording medium.

Preferably, the portable terminal further includes a third communication control unit exchanging data with the server managing the blood glucose level of the customer through a communication network, and the first control unit further provides to the third communication control unit the blood glucose level data received from the recording medium when transmitting the blood glucose level data to the server.

Preferably, the portable terminal further includes a display unit displaying the blood glucose level data, and the first control unit further applies to the display unit the blood glucose level data received from the recording medium when displaying the blood glucose data on the display unit.

According to the recording medium or the blood glucose monitoring system in accordance with the present invention, the blood glucose level can be measured using a portable terminal that can be connected to a network as a blood glucose monitoring apparatus. Therefore, the measured blood glucose level can be transmitted on the network using the portable terminal, and therefore, the blood glucose level data can be managed by a server installed at a medical institution, or the data stored in the server may be utilized for telemedicine.

Further, according to the recording medium or the blood glucose monitoring system of the present invention, the blood glucose level can be measured using a commercially available portable terminal as the blood glucose monitoring apparatus. Therefore, a dedicated blood glucose monitoring apparatus is unnecessary, a trouble such as failure of measurement resulting from malfunction of the dedicated blood glucose monitoring apparatus can be prevented, and the cost for the user can also be reduced, as the dedicated blood glucose monitoring apparatus is unnecessary.

According to the recording medium of the present invention, as the measured blood glucose level data is stored as it is on the recording medium, it becomes possible, when the recording medium is mounted to various apparatuses related to diabetes including a medicine (insulin) administering apparatus or a next generation pen device, to share the blood glucose level data among such apparatuses. Thus, very convenient treatment of diabetes such as artificial pancreas that integrates measurement of blood glucose level and administration of appropriate medicine becomes possible.

Further, according to the recording medium of the present invention, the recording medium itself does not includes the display device and the battery for driving the apparatus, and the display device and power supply battery of the portable terminal on which the recording medium is mounted are utilized. Thus, the recording medium itself can be made very compact, and a blood glucose monitoring apparatus, which is highly portable, is realized.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 6, 7 and 8 are first to third flow charts representing the process steps performed by the telemedicine system shown in FIG. 5.

DESCRIPTION OF THE PREFERRED EMBODIMENTS

Figure 1:
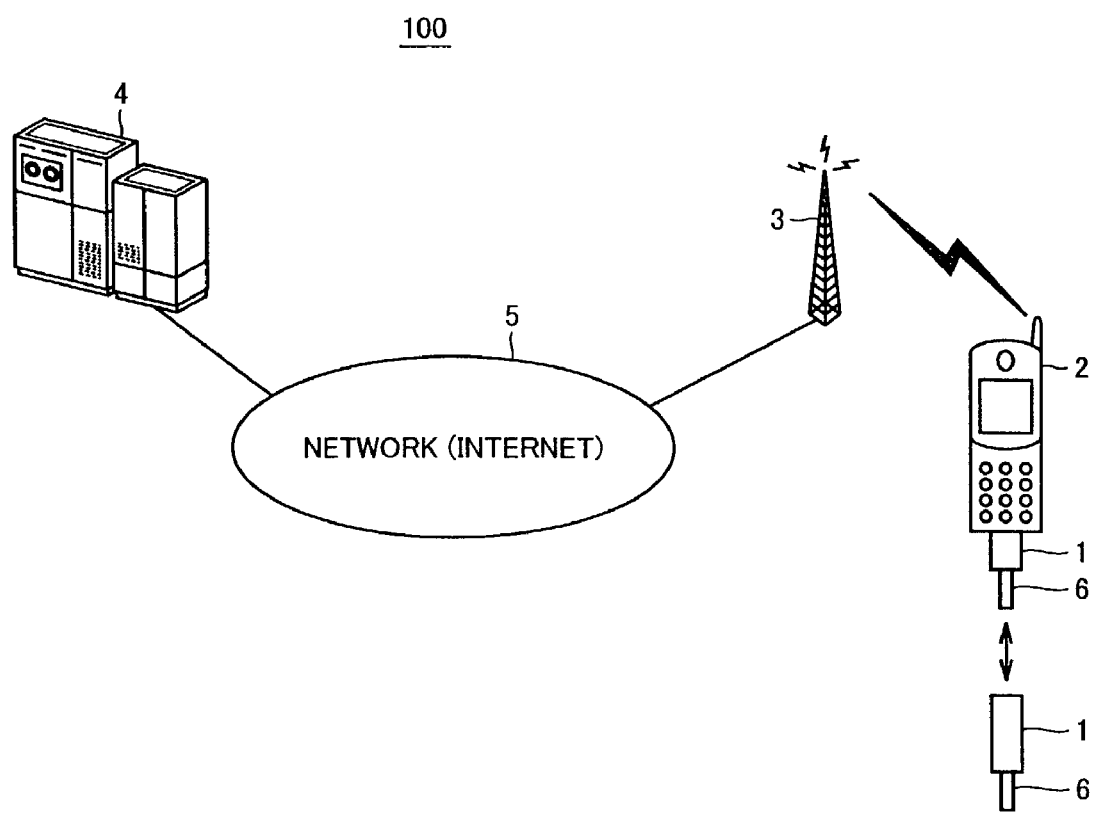
FIG. 1 is a schematic diagram representing the concept of the blood glucose monitoring system using the recording medium in accordance with the present invention.

Embodiments of the present invention will be described in detail with reference to the figures. In the figures, the same or corresponding portions are denoted by the same reference characters, and description thereof will not be repeated.

FIG. 1 shows a concept of a blood glucose monitoring system usable on a network, in which blood glucose level data measured by mounting the recording medium in accordance with the present invention on a portable terminal is transmitted from the portable terminal through a network to a server.

Referring to FIG. 1, the blood glucose monitoring system 100 includes a recording medium 1, a portable telephone 2, a wireless base station 3, a server 4, and a network 5 to which wireless base station 3 and server 4 are connected.

Recording medium 1 includes a blood glucose sensor for measuring glucose level of blood therein, and it is in compliance with the specification of a commercially available compact memory card that can be used mounted on a portable telephone or other personal digital assistant. Recording medium 1 is mounted on portable telephone 2 that accommodates the above described compact memory card, and operates while receiving power from portable telephone 2. Recording medium 1 monitors, while mounted on portable telephone 2, the blood glucose level by detecting a current that is generated in accordance with the level of glucose contained in the blood absorbed by a test paper 6, and stores and holds the blood glucose level data. The recording medium 1 stores the blood glucose level data in a non-volatile memory unit, and therefore the blood glucose level data is not lost even when recording medium 1 is detached from portable telephone 2 after measurement of the blood glucose level.

Recording medium 1 measures the blood glucose level when it is mounted on portable telephone 2, and transmits the blood glucose level data to portable telephone 2. Upon request from the user of portable telephone 2, recording medium 1 also transmits blood glucose level data measured in the past and stored and held therein to portable telephone 2.

Portable telephone 2 is a commercially available portable telephone connectable to a network, on which recording medium 1 can be mounted. When recording medium 1 is mounted, the portable telephone 2 supplies power for operation of recording medium 1, and displays on its display unit the blood glucose level data measured by recording medium 1. Further, portable telephone 2 transmits measured data of blood glucose level received from recording medium 1 through wireless base station 3 and network 5 to server 4.

Wireless base station 3 is a relay station connecting portable telephone 2 to network 5. Server 4 receives the blood glucose level data measured by recording medium 1 from portable telephone 2 through wireless base station 3 and network 5, and stores and manages the received blood glucose level data. Network 5 is one that is capable of bi-directional communication, such as the Internet.

In this manner, the personally measured blood glucose level data is transmitted through network 5 to server 4. Further, blood glucose monitoring system 100 may provide various services based on the blood glucose level data received by server 4.

Recording medium 1 used for blood glucose monitoring system 100 measures the blood glucose level of the blood on a test paper 6, with the test paper 6 to which obtained blood sample is applied being mounted on the medium.

Figure 2:
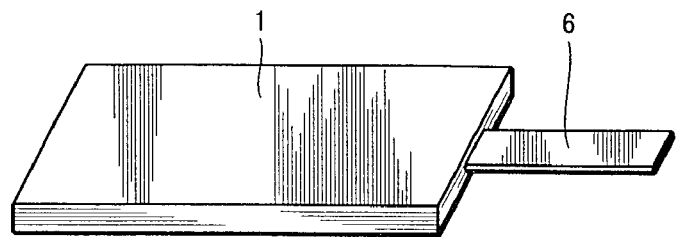
FIG. 2 shows an appearance of the recording medium used in the blood glucose monitoring system shown in FIG. 1.

FIG. 2 shows the manner how the test paper 6 is mounted on recording medium 1. The user of recording medium 1 puts a small amount of blood on a prescribed tip end of test paper 6, inserts the test paper 6 into an inlet port of recording medium 1, and blood glucose level is measured by recording medium 1 with test paper 6 inserted, mounted on portable telephone 2. A disposable test paper used for one measurement only is used as test paper 6. The blood sample is applied to test paper 6 by putting a puncture needle on one's finger tip, for example, by a dedicated puncture device having a puncture needle at a tip end, thus obtaining a small amount of blood.

Figure 3:
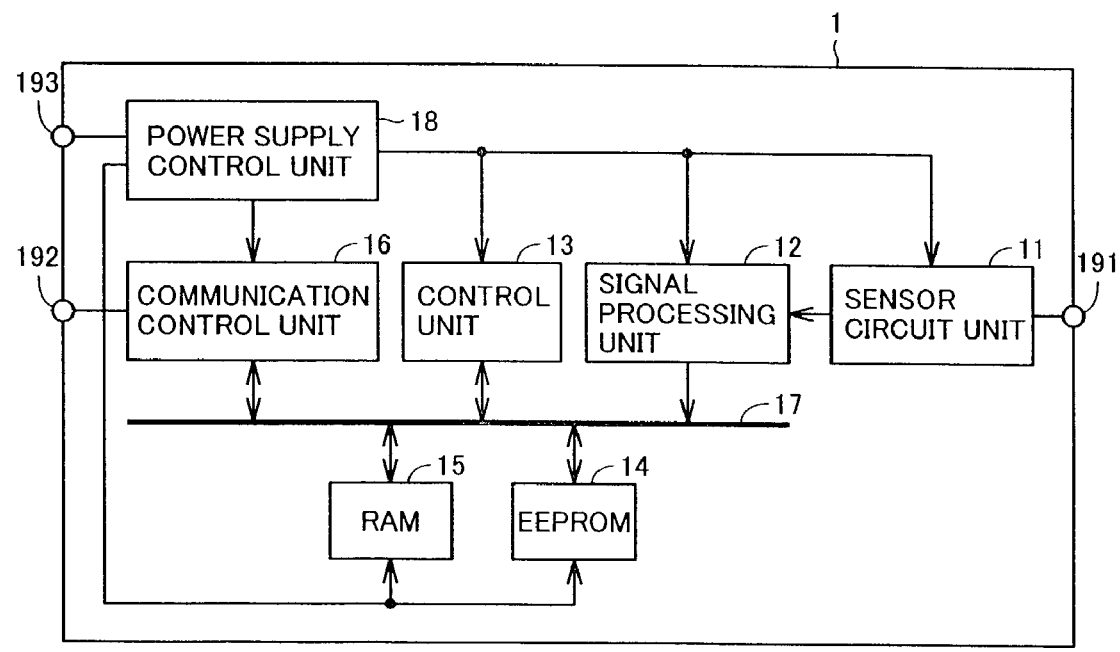
FIG. 3 is a block diagram representing a configuration of the recording medium used in the blood glucose monitoring system shown in FIG. 1.

Referring to FIG. 3, recording medium 1 includes a sensor circuit unit 11, a signal processing unit 12, a control unit 13, an EEPROM (Electrically Erasable Programmable Read Only Memory) 14 as a non-volatile memory unit, an RAM (Random Access Memory) 15 as a volatile memory unit, a communication control unit 16, a bus 17 and a power supply control unit 18. Recording medium 1 further includes an inlet port 191, a data input/output terminal 192 and a power supply terminal 193.

Inlet port 191 is for inserting test paper 6 for mounting the test paper 6 on which obtained blood is applied, on recording medium 1.

Data input/output terminal 192 is joined to a data input/output terminal of portable telephone 2, and exchanges data between recording medium 1 and portable telephone 2.

Power supply terminal 193 is joined to a power supply output terminal of portable telephone 2, and power is supplied from power supply unit of portable telephone 2 to power supply control unit 18.

Sensor circuit 11 uses, for example, an enzyme electrode having glucose dehydrogenase fixed with a redox mediator interposed, as an electrode, and generates a current from enzyme reaction between glucose in the blood and glucose dehydrogenase. Thus, the recording medium 1 in accordance with the present invention is capable of detecting blood glucose from a very small amount of blood.

Signal processing unit 12 converts the current generated from sensor circuit unit 11 to a digital signal and outputs the same.

Control unit 13 is, for example, an MPU (Micro Processing Unit), that performs conversion of the data converted to digital data and output from signal processing unit 12 to blood glucose level data, writing of blood glucose level data to EEPROM14 storing the blood glucose level data and reading of the blood glucose level data from EEPROM14, and transmission of read glucose level data to portable telephone 2 on which recording medium 1 is mounted.

EEPROM14 is an electrically erasable and programmable non-volatile flash memory, which stores blood glucose levels of a plurality of measurements.

RAM 15 is a work memory for control unit 13.

Communication control unit 16 exchanges data between recording medium 1 and potable telephone 2 through data input/output terminal 192.

Bus 17 is a data communication path between each of sensor circuit unit 11, signal processing unit 12, control unit 13, EEPROM 14, RAM 15 and communication control unit 16.

Power control unit 18 receives power from portable telephone 2 through power supply terminal 193, as recording medium 1 itself does not have any power source, and supplies a prescribed power for operation, to sensor circuit unit 11, signal processing unit 12, control unit 13, EEPROM 14, RAM 15 and communication control unit 16.

When test paper 6 with obtained blood applied is inserted to inlet port 191 of recording medium 1, sensor circuit unit 11 detects the current generated in accordance with the blood glucose level of the blood on test paper 6, and outputs the detected current to signal processing unit 12. Signal processing unit 12 converts the current generated by sensor circuit unit 11 to digital data and outputs to control unit 13. Control unit 13 temporarily writes the data received from signal processing unit 12 to RAM 15, reads the data from RAM 15, converts the read data to blood glucose level data, and writes to EEPROM 14.

Control unit 13 transmits the blood glucose level data to portable telephone 2 through communication control unit 16, so as to display the result of measurement of blood glucose level on a display unit of portable telephone 2, or to transmit the blood glucose level data from portable telephone 2 to server 4 through network 5. Further, upon reception of a request for transmitting blood glucose level data of the past necessary for displaying the progress of the blood glucose level from portable telephone 2, control unit 13 successively reads the past blood glucose level data from EEPROM 14 in order, writes the read data in RAM 15 temporarily and reads the data from RAM 15 and transmits to portable telephone 2 through communication control unit 16.

Figure 4:
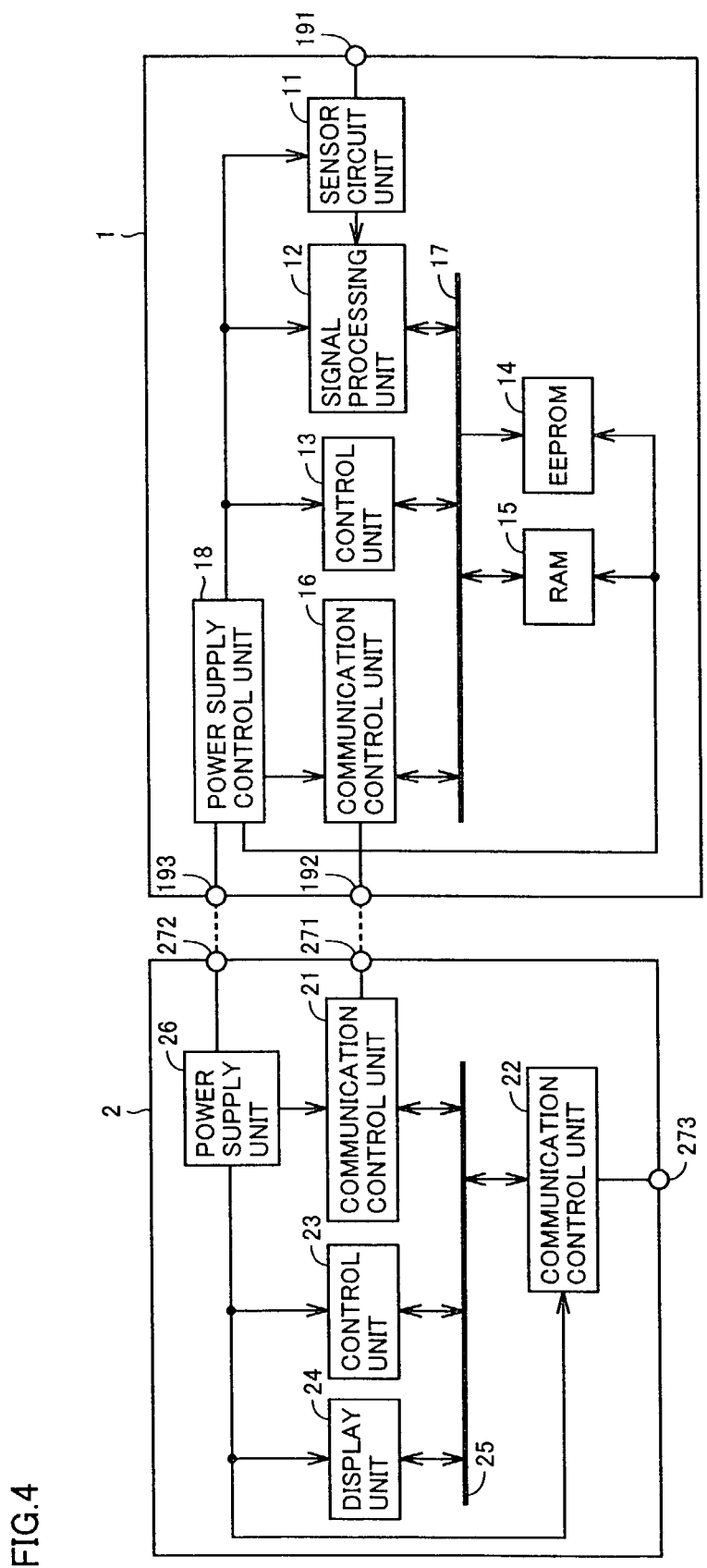
FIG. 4 is a block diagram representing a configuration of a monitoring system including a portable telephone and a recording medium, used in the blood glucose monitoring system shown in FIG. 1.

FIG. 4 shows a configuration of the blood glucose monitoring system including recording medium 1 and portable telephone 2. Portable telephone 2 includes communication control units 21, 22, a control unit 23, a display unit 24, a bus 25 and a power supply unit 26. Portable telephone 2 further includes a data input/output terminal 271, a power supply terminal 272 and an antenna 273.

Data input/output terminal 271 is joined to data input/output terminal 192 of recording medium 1, and exchanges data between recording medium 1 and portable telephone 2.

Power supply terminal 272 is joined to power supply terminal 193 of recording medium 1, and supplies power from power supply unit 26 of portable telephone 2 to power supply control unit 18 of recording medium 1.

Antenna 273 transmits blood glucose level data measured by recording medium 1 to wireless base station 3. Through wireless base station 3 and network 5, the blood glucose level data is transmitted to server 4.

Communication control unit 21 exchanges data between portable telephone 2 and recording medium 1 through data input/output terminal 271.

Communication control unit 22 exchanges data between portable telephone 2 and wireless base station 3 connected to network 5, through an antenna 273.

Control unit 23 is implemented by an MPU, for example, which controls communication control units 21, 22 and display unit 24, to perform transmission/reception of data to and from the mounted recording medium 1, transmission/reception of data to and from server 4 through wireless base station 3 and network 5, and display of blood glucose level data on display unit 24, which will be described later.

Display unit 24 displays the blood glucose level data measured by recording medium 1.

Bus 25 is a data communication path between each of communication control units 21, 22, control unit 23 and display unit 24.

Power supply unit 26 supplies power for operation of communication control units 21, 22, control unit 23 and display unit 24. Power supply unit 26 further supplies power for operation of recording medium 1 to power supply control unit 18 of recording medium 1, through power supply terminal 272 and power supply terminal 193 of recording medium 1.

When test paper 6 with obtained blood applied is inserted to inlet port 191 of recording medium 1, sensor circuit unit 11 detect a current generated in accordance with the glucose level of the blood on test paper 6, and outputs the current to signal processing unit 12. Signal processing unit 12 converts the current output from sensor circuit unit 11 to digital data and outputs to control unit 13. Control unit 13 temporarily writes the data received from signal processing unit 12 to RAM15, and reads data from RAM15, converts to blood glucose level data, and writes the converted data to EEPROM14. Control unit 13 transmits the blood glucose level data to portable telephone 2 through communication control unit 16, in order to display the measured blood glucose level data on display unit 24 of portable telephone 2, or to transmit the blood glucose level data from portable telephone 2 to server 4 through antenna 273, wireless base station 3 and network 5.

Upon reception of blood glucose level data from recording medium 1 through communication control unit 21, control unit 23 of portable telephone 2 outputs the blood glucose level data to display unit 24, and display unit 24 displays the blood glucose level data. Control unit 23 transmits the received blood glucose level data to communication control unit 22, and instructs to transmit the data to server 4. Communication control unit 22 transmits blood glucose level data to wireless base station 3 through antenna 273, and the blood glucose level data is transmitted through wireless base station 3 and network 5 to server 4.

Upon reception of a request for transmitting past blood glucose level data necessary for displaying the progress of the blood glucose level from portable telephone 2 through communication control unit 16, control unit 13 of recording medium 1 successively reads the blood glucose level data of the past from EEPROM 14 and temporarily writes to RAM15, and reads the data from RAM15 and transmits to portable telephone 2 through communication control unit 16. Upon reception of the past blood glucose level data from recording medium 1 through communication control unit 21, control unit 23 of portable telephone 2 successively outputs the blood glucose level data on display unit 24, and display unit 24 displays the progress of the past blood glucose level.

A telemedicine system using a portable medical terminal would be described as an embodiment utilizing recording medium 1 of the present invention.

Figure 5:
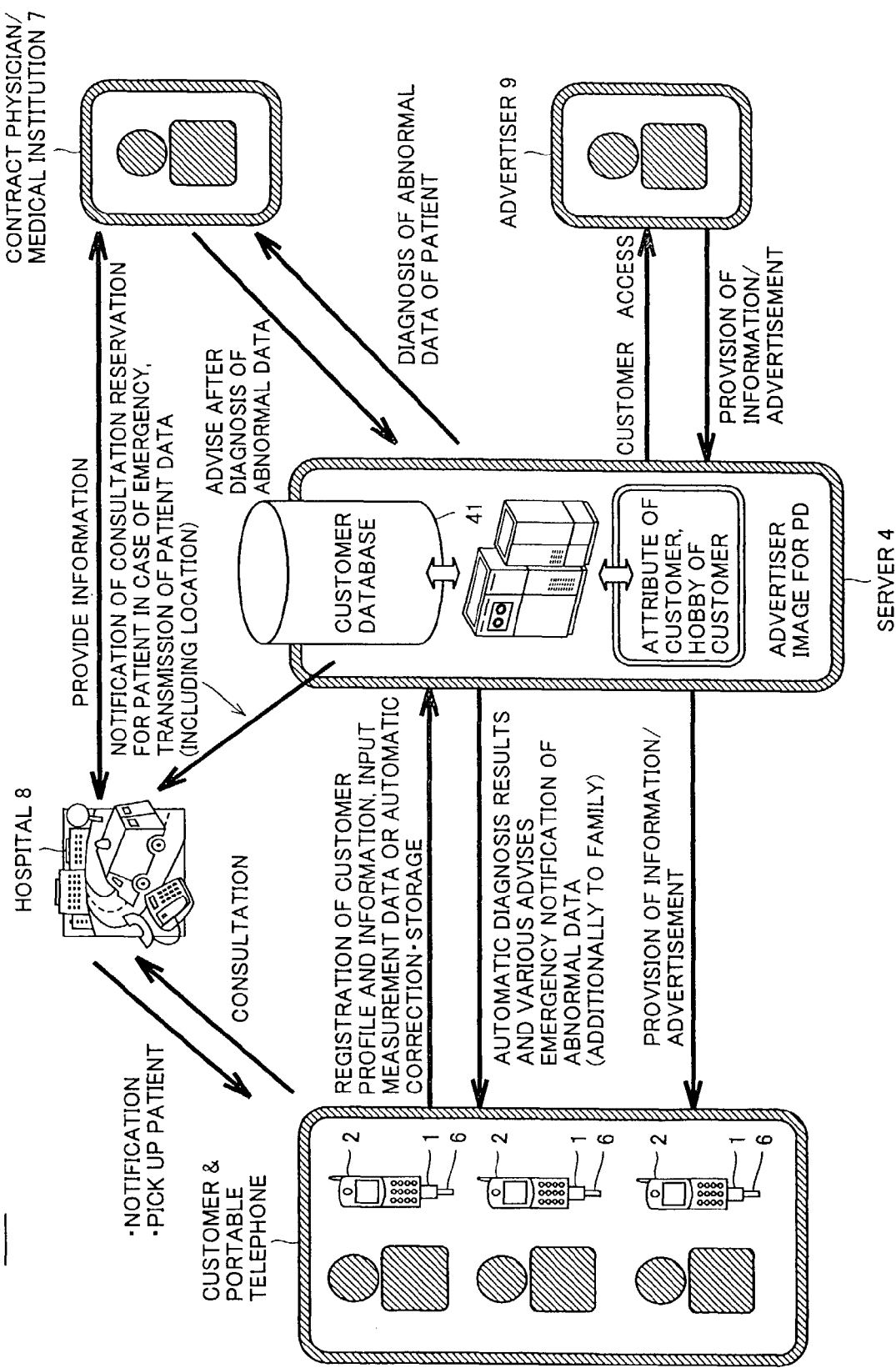
FIG. 5 is a schematic diagram representing a concept of the telemedicine system, using the blood glucose monitoring system shown in FIG. 1.

FIG. 5 is a schematic diagram representing a telemedicine system 200. Referring to FIG. 5, telemedicine system 200 includes portable telephone 2 on which recording medium 1 is mounted, and server 4 storing customer information on a data base. Portable telephone 2 and server 4 are connected by network 5 and wireless base station 3 described with reference to FIG. 1. In telemedicine system 200, a contract physician/medical institution 7, a hospital 8 and an advertiser 9 are connected to server 4 or potable telephone 2 through network 5, by using a portable telephone or personal computer of its own.

Server 4 has a customer database 41 holding data of customers of telemedicine system 200, and receives, in advance, profile data of the customers from portable telephones 2 of customers and stores the received data in customer database 41. Further, server 4 performs analysis and diagnosis on blood glucose level data transmitted from a portable telephone 2, and transmits to portable telephone 2 the result of diagnosis and various advise information. Further, when the blood glucose level data received from portable telephone 2 is determined to be abnormal, server 4 transmits the blood glucose level data to contract physician/medical institution 7, as will be described later. When an emergency information that the blood glucose level data received from portable telephone 2 is abnormal and urgent response is necessary is received from contract physician/medical institution 7, server 4 makes a consultation reservation of the customer at hospital 8 near the customer, or transmits customer data stored in customer data base 41, in accordance with an instruction from contract physician/medical institution 7 included in the emergency information.

Contract physician/medical institution 7 represents a contract physician or a medical institution having a contract with a managing company operating the telemedicine system 200, and the physician or institution performs analysis and diagnosis on the blood glucose level data received from server 4, and returns the result of diagnosis and various advises to server 4. When the contract physician/medical institution 7 determines that an urgent response is necessary as a result of analyzing blood glucose level data, the physician or institution transmits emergency information to server 4 including an instruction to the customer to have a consultation at hospital 8 nearby, or an instruction to transfer customer data to hospital 8.

Hospital 8 receives consultation reservation of a customer who needs urgent consultation as well as the customer data from server 4, reserves consultation of the customer, and contact to the customer, urging visit to the hospital for consultation.

The customer of telemedicine system 200, who is the user of portable telephone 2, obtains blood sample and puts the blood on test paper 6, inserts the test paper to recording medium 1, and measures the blood glucose level, by mounting recording medium 1 on portable telephone 2. The customer connects portable telephone 2 to server 4, and transmits the measured blood glucose level data to server 4. Alternatively, portable telephone 2 may be adopted to automatically connect to server 4 and to transmit blood glucose level data, so as to prevent failure to transmit the measured blood glucose level data.

Server 4 stores the blood glucose level data received from portable telephone 2 in customer database 41, in association with profile data of the customer. The profile data of the customer includes information identifying the customer such as name, age and sex, clinical history of the customer, past diagnosis, contact address in case of emergency, and contact address of the customer's family in case of emergency. Server 4 makes a diagnosis on the blood glucose level data of the customer received from portable telephone 2, and transmits the result of diagnosis and various advise information in accordance with the result of diagnosis, to portable telephone 2. Further, when it is determined that the blood glucose level data of the customer is abnormal, server 4 transmits the abnormal blood glucose level data to contract physician/medical institution 7, and asks for diagnosis on the blood glucose level data.

Contract physician/medical institution 7 performs analysis and diagnosis of the abnormal blood glucose level data, and transmits the result of diagnosis and related advice information to server 4. Upon reception of the result of diagnosis and advise information on the abnormal blood glucose level data from contract physician/medical institution 7, server 4 transmits the result and information to portable telephone 2. When the contract physician/medical institution 7 determines, as a result of diagnosis on the abnormal blood glucose level data, that an urgent response is necessary, the physician or institution transmits emergency information to server 4, including an instruction for the customer to have a consultation at a hospital 8 nearby, in addition to the result of diagnosis and the advise information.

Upon reception of the emergency information from contract physician/medical institution 7, server 4 transmits an emergency report based on the emergency information to portable telephone 2, as well as to the contact address of the customer's family stored in the customer database. Further, server 4 transmits information including consultation reservation of the customer, profile data of the customer, the abnormal blood glucose level data measured this time, and a result of diagnosis made by the contract physician/medical institution 7, to hospital 8 nearby, designated by contract physician/medical institution 7.

Upon reception of the information of a customer requiring urgent consultation from server 4, the hospital 8 reserves consultation, in accordance with the instruction from contract physician/medical institution 7 and makes a contact to the customer, or when it is impossible for the customer to visit the hospital 8 by himself/herself, delivers an ambulance to the customer. Thus, the customer has a consultation at the hospital 8.

A process flow of the above described telemedicine system 200 will be described in detail with reference to FIGS. 6 to 8.

Figure 6:
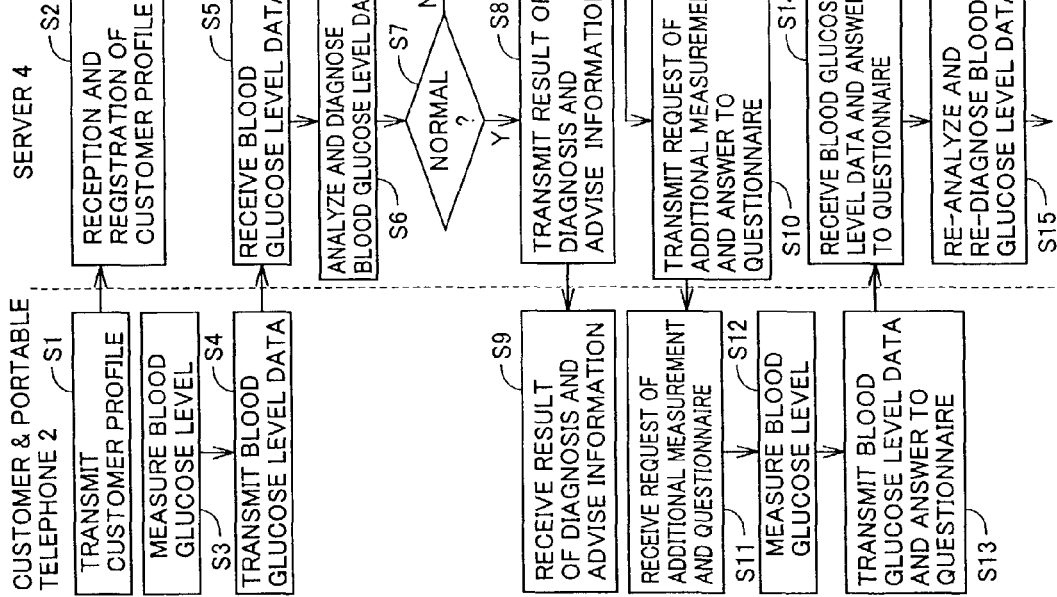

Referring to FIG. 6, the customer receiving the service of telemedicine system 200 transmits, in advance, profile data of the customer from portable telephone 2 to server 4 (step S1), and server 4 registers the profile data of the customer received from portable telephone 2 in a customer data server 41 (step S2). The customer puts the obtained blood sample on test paper 6, inserts the test paper 6 to recording medium 1, and mounts the recording medium 1 on portable telephone 2 to measure the blood glucose level (step S3). When measurement of the blood glucose level ends, the customer accesses from portable telephone 2 to server 4, and transmits the measured blood glucose level data to server 4 (step S4).

Server 4 receives the blood glucose level data from portable telephone 2 (step S5), analyzes the blood glucose level data, and makes a diagnosis of "normal", "slightly problematic", "problematic" and "abnormal" (step S6).

When it is diagnosed that the received blood glucose level data is "normal" (step S7), the server 4 transmits the result of diagnosis and various advise information based on the analysis/diagnosis to portable telephone 2 (step S8). The customer, who have sent the blood glucose level data from portable telephone 2, receives the result of diagnosis and advise information on the transmitted blood glucose level data, from server 4 (step S9).

When it is diagnosed that the blood glucose level data is not "normal" (step S7), the server 4 further requests additional measurement of the blood glucose level, and an answer to a questionnaire transmitted as attached, to portable telephone 2 (step S10).

When the customer receives at portable telephone 2 the request of additional measurement and attached questionnaire from server 4 (step S11), the customer again obtains a blood sample, applies it to test paper 6, inserts the test paper 6 to recording medium 1, mounts recording medium 1 on portable telephone 2, and measures the blood glucose level (step S12). Then, the customer accesses from portable telephone 2 to server 4, and transmits the re-measured blood glucose level data and the answer to the questionnaire received from server 4, to server 4 (step S13).

Upon reception of the re-measured blood glucose level data and the answer to the questionnaire from portable telephone 2 (step S14), server 4 again analyzes the received blood glucose level data, and again makes a diagnosis of "normal", "slightly problematic", "problematic" and "abnormal" (step S15).

Referring to FIG. 7, when the re-measured blood glucose level data is diagnosed as not "abnormal" (step S16), the server 4 transmits the result of diagnosis and various advise information based on the analysis/diagnosis to portable telephone 2 (step S17). The customer who again transmitted the blood glucose level data from portable telephone 2 receives the result of diagnosis and the advice information on the re-transmitted blood glucose level data from server 4 (step S18).

When the read glucose level data is diagnosed again as "abnormal" (step S16), the server 4 determines that consultation with a physician is necessary, and transmits the blood glucose level data that is diagnosed to be abnormal to a contract physician/medical institution 7 that has a contract to make diagnoses on the abnormal blood glucose level data (step S19). When the contract physician/medical institution 7 receives the measurement data diagnosed to be abnormal from server 4 (step S20), a contract physician or a physician at the contract medical institution performs analysis and diagnosis of the blood glucose level data (step S21).

Based on the result of diagnosis, when the contract physician or the physician in charge determines that emergency measures are not necessary (step S22), the contract physician or the physician in charge returns the result of diagnosis and advice information to server 4 (step S23). Upon reception of the result of diagnosis and advise information on the abnormal blood glucose level data from contract physician/medical institution 7 (step S24), server 4 stores the result of diagnosis and advise information in a customer data base of server 4 in association with the customer profile data, and transmits the result of diagnosis and advise information to portable telephone 2 (step S25). The customer, who has re-transmitted the blood glucose level data from portable telephone 2, receives at portable telephone 2, the result of diagnosis and advise information from the physician, from server 4 (step S26).

When the contract physician/medical institution 7 determines, based on the result of diagnosis of the blood glucose level data received from the server 4, that an emergency measures must be taken (step S22), the contract physician/medical institution 7 transmits, in addition to the result of diagnosis and advise information, specific emergency information including an instruction of a consultation at a hospital 8 in the customer's neighborhood (step S27). Upon reception from the emergency information from contract physician/medical institution 7 (step S28), server 4 transmits an emergency notification to portable telephone 2, notifying an urgent consultation at hospital 8 is necessary (step S29). The customer who has re-transmitted the blood glucose level data receives the emergency notification from server 4, at portable telephone 2 (step S30). Here, the server 4 may be adopted to read a contact address of the customer's family included in the customer profile data of data base 41, and may notify the emergency to the family of the customer.

Referring to FIG. 8, the server 4 that has transmitted the emergency notification to portable telephone 2 transmits, based on the emergency information received from contract physician/medical institution 7, consultation reservation for the customer, customer data stored in customer data base 41, the abnormal blood glucose level data measured this time, the result of diagnosis made by the contract physician/medical institution 7 and the like, to hospital 8 in the customer's neighborhood designated by contract physician/medical institution 7 (step S31). Receiving the consultation reservation for the customer and customer data and the like (step S32), the hospital 8 reserves a consultation for the customer, and contacts to the portable telephone 2 to urge the customer to have consultation immediately (step S33). The customer, receiving the request for consultation from hospital 8 (step S34), visits hospital 8 and receives consultation (step S35).

When it is determined from the customer data received from server 4 and the like that it is impossible for the customer to visit hospital 8 by himself/herself, hospital 8 may deliver an ambulance to the address of the customer, based on the customer data. Hospital 8 transmits the result of consultation for the customer to the contract physician/medical institution 7 that has made initial diagnosis (step S36), and the contract physician/medical institution 7 receives the result of consultation for the customer to whom consultation with hospital 8 was instructed, from hospital 8 (step S37).

In this manner, a telemedicine system is realized using the recording medium 1 in accordance with the present invention and the portable telephone 2 connectable to the network and functions as a blood glucose monitoring apparatus with recording medium 1 mounted thereon.

Telemedicine system 200 further provides services including provision of information on medicine and medical equipment to customer, and advertisement of companies manufacturing and selling such medicine and medical equipment.

Again referring to FIG. 8, an advertiser 9 request customer data from server 4, using a personal computer connected to network 5, for example (step S41). Upon reception of the request for customer data from advertiser 9 (step S42), server 4 reads the customer data from customer data base 41 and transmits the read data to advertiser 9 (step S43).

Receiving the customer data from server 4 (step S44), advertiser 9 transmits, based on the blood glucose level data, medical history, past diagnosis and the like of the customer, information on appropriate medicine or medical equipment and company advertisement of advertiser 9, to server 4 (step S45).

When server 4 receives from advertiser 9 the information on medicine or medical equipment for the customer and the company advertisement of the advertiser (step S46), the server 4 transmits the received information and the customer advertisement to portable telephone 2 of the customer (step S47). The customer receives the information of the medicine or medical equipment suitable for him/her and company advertisement of the company providing the information on portable telephone 2 (step S48).

Though not shown, utilizing telemedicine system 200, recording medium 1 may be mounted on various devices related to diabetes such as a medicine (insulin) administering device or a next generation pen device, so that measurement of blood glucose level and administration of medicine can be integrated. More specifically, server 4 calculates the dose of medicine to be administered to the customer, based on the blood glucose level data transmitted from portable telephone 2 and customer data stored in customer data base 41. Server 4 then transmits the dose data related to the calculated dose to portable telephone 2.

Upon reception of the dose data of the medicine that corresponds to the measured blood glucose level data from server 4, portable telephone 2 transmits the received dose data to recording medium 1, and recording medium 1 records and holds the received dose data. The customer, receiving the dose data of medicine at the recording medium 1 from server 4, mounts the recording medium 1 to a medicine administering device that can accommodate the recording medium 1. Then, the medicine is administered to the customer, based on the dose data of medicine recorded on recording medium 1.

The portable telephone 2 described in the embodiments above may be a PDA (Personal Digital Assistance), a portable personal computer, a digital camera, a portable television or other communication terminal, provided that it can accommodate the recording medium 1 and connectable to a network.

According to the embodiments of the present invention, as the recording medium 1 is mounted on a network connectable portable telephone 2 to be used as a blood glucose monitoring apparatus, it becomes possible for a diabetes patient who needs monitoring of blood glucose level to transmit the measured blood glucose level data directory from portable telephone 2 through network 5 to a server 4 that is installed at a medical institution or the like, and to receive various medical services from server 4, through network 5.

Further, according to the embodiments of the present invention, as the blood glucose level can be monitored using recording medium 1 mounted on a commercially available portable telephone 2 as a blood glucose monitoring apparatus, it becomes unnecessary to have a dedicated blood glucose monitoring apparatus. Therefore, a trouble such as failure in monitoring resulting from malfunction of the dedicated blood glucose monitoring apparatus can be prevented, and the cost can also be reduced, as the dedicated blood glucose monitoring apparatus is unnecessary.

Further, according to the embodiments of the present invention, as measured blood glucose level data is directly recorded on recording medium 1, when recording medium 1 is mounted on various devices related to diabetes such as medicine (insulin) administering device or a next generation pen device, the blood glucose level data can be shared among the devices, and very convenient treatment of diabetes such as artificial pancreas that has the functions of measuring blood glucose level and administration of medicine integrated becomes possible.

Further, according to the embodiments of the present invention, the display unit of portable telephone 2 on which recording medium 1 is mounted is used as the display unit for displaying the measured blood glucose level, and the power supply battery of portable telephone 2 on which recording medium 1 is mounted is used as an operational power supply of recording medium 1, and therefore, the recording medium 1 itself does not require any display unit or a power supply battery. Therefore, recording medium 1 itself can be made very compact, and a blood glucose monitoring apparatus which is highly portable is realized.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A recording medium operating mounted on a portable terminal capable of supplying power, comprising:
    a communication control unit exchanging data with said portable terminal;
    an inlet port for inserting a test paper configured for mounting said test paper on which taken blood is applied
    a sensor circuit unit generating a current from a blood glucose level of blood applied to said test paper mounted on said inlet port;
    a signal processing unit converting said generated current to a digital data and outputting the data;
    an electrically erasable and programmable non-volatile memory unit storing blood glucose level data converted based on the data output from said signal processing unit;
    a control unit converting the data output from said signal processing unit to said blood glucose level data, writing the converted data to said memory unit, reading said blood glucose level data from said memory unit and transmitting the data to said portable terminal through said communication control unit; and
    a power supply control unit receiving power from said portable terminal and supplying power to said sensor circuit unit, said signal processing unit, said memory unit, said communication control unit and said control unit; wherein
    said communication control unit, said inlet port, said sensor circuit unit, said signal processing unit, said memory unit, said control unit and said power supply control unit are integrally configured.

2. The recording medium according to claim 1, wherein said portable terminal transmits said measured blood glucose level data to a server managing blood glucose level of a customer, through a communication network.

3. The recording medium according to claim 1, wherein said portable terminal displays said measured blood glucose level data.

4. The recording medium according to claim 1, wherein said portable terminal is one of a portable telephone, a personal digital assistant and a portable personal computer.

5. A blood glucose monitoring system including
    a portable terminal, and
    a recording medium operating mounted on said portable terminal, wherein
    said portable terminal includes
        a first communication unit exchanging data with said recording medium,
        a power supply unit supplying power to said recording medium and
        a first control unit;
    said recording medium includes
        a second communication control unit exchanging data with said portable terminal,
        an inlet port for inserting a test paper configured for mounting said test paper on which taken blood is applied,
        a sensor circuit unit generating a current from blood glucose level of blood applied to said test paper mounted on said inlet port,
        a signal processing unit converting said generated current to digital data and outputting the digital data,
        an electrically erasable and programmable non-volatile memory unit storing blood glucose level data converted based on the data output from said signal processing unit,
        a second control unit converting the data output from said signal processing unit to said blood glucose level data and writing in said memory unit, reading said blood glucose level data from said memory unit and transmitting the read data to said portable terminal through said second communication control unit, and
        a power supply control unit receiving power from said portable terminal and supplying power to said sensor circuit unit, said signal processing unit, said memory unit, said second communication control unit and said second control unit; and
    said first control unit controls said first communication control unit when the blood glucose data is received from said recording medium, and
    said second communication control unit, said inlet port, said sensor circuit unit, said signal processing unit, said memory unit, said second control unit, and said power supply control unit that implement said recording medium are integrally configured.

6. The blood glucose monitoring system according to claim 5, wherein
    said portable terminal further includes a third communication control unit exchanging data with a server managing blood glucose level of a customer through a communication network; and
    said first control unit further applies the blood glucose level data received from said recording medium to said third communication control unit, when transmitting said blood glucose level data to said server.

7. The blood glucose monitoring system according to claim 5, wherein
    said portable terminal further includes a display unit displaying said blood glucose level data; and
    said first control unit further applies the blood glucose level data received from said recording medium to said display unit, when displaying said blood glucose level data on said display unit.

8. The blood glucose monitoring system according to claim 5, wherein
    said portable terminal is one of a portable telephone, a personal digital assistant and a portable personal computer.

9. The recording medium according to claim 1, further comprising:
    a data input/output terminal to be joined to another data input/output terminal of said portable terminal, wherein, said communication control unit exchanges data with said portable terminal through said data input/output terminal.

10. The blood glucose monitoring system according to claim 5, wherein,
said portable terminal further include a first data input/output terminal,
said first communication unit exchanges data with said recording medium through said first data input/output terminal,
said recording medium further includes:
a second data input/output terminal to be joined to said first data input/output terminal of said portable terminal, and
said second communication control unit exchanges data with said portable terminal through said second data input/output terminal.

11. A recording device mountable on a portable terminal having a power supply that includes:
an inlet port for inserting a test paper configured for mounting said test paper on which taken blood is applied;
a sensor circuit unit generating a current from a blood glucose level of blood applied to said test paper mounted on said inlet port;
a signal processing unit digitizing the generated current to a digital data and outputting the digital data to a control unit;
an electrically erasable and programmable non-volatile memory unit operably connected to the control unit;
a communication unit operably connected to the control unit for exchanging data with the portable terminal; and
a power supply control unit operably connected to the power supply and supplying power to the sensor circuit unit, the signal processing unit, the memory unit, the communication unit and the control unit; wherein
the control unit converts the digital data to blood glucose level data, stores blood glucose level data in the memory unit, reads stored blood glucose level data from the memory unit and transmits blood glucose level data to the portable terminal through the communication unit; and
said inlet port, said sensor circuit unit, said signal processing unit, said memory unit, said communication unit, said power supply control unit, and said control unit are integrally configured.

12. The recording medium according to claim 1, wherein said sensor circuit unit includes an enzyme electrode and generates a current from enzyme reaction between glucose in the blood and said enzyme electrode.

13. The blood glucose monitoring system according to claim 5, wherein said sensor circuit unit includes an enzyme electrode and generates a current from enzyme reaction between glucose in the blood and said enzyme electrode.

14. The recording device according to claim 11, wherein said sensor circuit unit includes an enzyme electrode and generates a current from enzyme reaction between glucose in the blood and said enzyme electrode.

\* \* \* \* \*